(12) United States Patent
Wallace

(10) Patent No.: US 10,667,873 B2
(45) Date of Patent: Jun. 2, 2020

(54) SURGICAL END EFFECTORS WITH MECHANICAL ADVANTAGE

(71) Applicant: Covidien LP, Mansfield, MA (US)

(72) Inventor: Daniel Wallace, Santa Cruz, CA (US)

(73) Assignee: Covidien LP, Mansfield, MA (US)

( * ) Notice: Subject to any disclaimer, the term of this patent is extended or adjusted under 35 U.S.C. 154(b) by 209 days.

(21) Appl. No.: 15/737,433

(22) PCT Filed: Jun. 21, 2016

(86) PCT No.: PCT/US2016/038458
§ 371 (c)(1),
(2) Date: Dec. 18, 2017

(87) PCT Pub. No.: WO2016/209788
PCT Pub. Date: Dec. 29, 2016

(65) Prior Publication Data
US 2018/0153629 A1 Jun. 7, 2018

Related U.S. Application Data

(60) Provisional application No. 62/183,383, filed on Jun. 23, 2015.

(51) Int. Cl.
*A61B 34/30* (2016.01)
*A61B 34/00* (2016.01)
*A61B 17/29* (2006.01)

(52) U.S. Cl.
CPC .............. *A61B 34/30* (2016.02); *A61B 17/29* (2013.01); *A61B 34/70* (2016.02); *A61B 34/71* (2016.02);
(Continued)

(58) Field of Classification Search
CPC ......... A61B 34/30; A61B 17/29; A61B 34/71; A61B 2017/2934; A61B 2017/2933;
(Continued)

(56) References Cited

U.S. PATENT DOCUMENTS 5,207,114 A 5/1993 Salisbury, Jr. et al.
5,562,701 A 10/1996 Huitema et al.
(Continued)

FOREIGN PATENT DOCUMENTS

CN 103565515 A 2/2014
EP 2687177 A2 1/2014
(Continued)

OTHER PUBLICATIONS

Supplementary European Search Report issued in European Application No. 16815122.3 dated Jan. 23, 2019, 8 pages.
(Continued)

*Primary Examiner* — Julian W Woo
(74) *Attorney, Agent, or Firm* — Carter, DeLuca & Farrell, LLP

(57) ABSTRACT

A robotic surgical system includes a pair of movable members and a pair of jaw members. The movable members include drive and guide pins that are received within holes and slots defined by the jaw members. The jaw members are movable relative to one another in response to movement of the movable members.

22 Claims, 9 Drawing Sheets

(52) U.S. Cl.
CPC .............. *A61B 2017/2933* (2013.01); *A61B 2017/2934* (2013.01); *A61B 2017/2936* (2013.01); *A61B 2017/2939* (2013.01); *A61B 2017/2944* (2013.01)

(58) Field of Classification Search
CPC .... A61B 2017/2944; A61B 2017/2939; A61B 2017/2936; A61B 34/70
See application file for complete search history.

(56) References Cited

U.S. PATENT DOCUMENTS

| | | | |
|---|---|---|---|
| 5,710,870 A | 1/1998 | Ohm et al. | |
| 5,752,973 A * | 5/1998 | Kieturakis | A61B 17/29 606/205 |
| 6,132,441 A | 10/2000 | Grace | |
| 6,206,903 B1 | 3/2001 | Ramans | |
| 6,312,435 B1 * | 11/2001 | Wallace | A61B 34/70 606/130 |
| 6,394,998 B1 | 5/2002 | Wallace et al. | |
| 6,554,844 B2 | 4/2003 | Lee et al. | |
| 6,582,451 B1 | 6/2003 | Marucci et al. | |
| 6,676,684 B1 | 1/2004 | Morley et al. | |
| 6,840,938 B1 | 1/2005 | Morley et al. | |
| 6,994,708 B2 | 2/2006 | Manzo | |
| 7,090,689 B2 | 8/2006 | Nagase et al. | |
| 7,101,363 B2 | 9/2006 | Nishizawa et al. | |
| 7,105,000 B2 | 9/2006 | McBrayer | |
| 7,422,592 B2 | 9/2008 | Morley et al. | |
| 7,566,334 B2 | 7/2009 | Christian et al. | |
| 7,608,083 B2 | 10/2009 | Lee et al. | |
| 7,699,835 B2 * | 4/2010 | Lee | A61B 17/062 606/1 |
| 7,744,608 B2 | 6/2010 | Lee et al. | |
| 7,914,522 B2 | 3/2011 | Morley et al. | |
| 8,245,594 B2 | 8/2012 | Rogers et al. | |
| 8,262,655 B2 | 9/2012 | Ghabrial et al. | |
| 8,277,443 B2 | 10/2012 | Jinno | |
| 8,333,780 B1 | 12/2012 | Pedros et al. | |
| 8,343,141 B2 | 1/2013 | Madhani et al. | |
| 8,394,120 B2 | 3/2013 | Krzyzanowski | |
| 8,398,619 B2 | 3/2013 | Doyle et al. | |
| 8,398,634 B2 | 3/2013 | Manzo et al. | |
| 8,523,900 B2 | 9/2013 | Jinno et al. | |
| 8,540,748 B2 | 9/2013 | Murphy et al. | |
| 8,568,443 B1 | 10/2013 | Jackman et al. | |
| 8,663,270 B2 | 3/2014 | Donnigan et al. | |
| 8,828,023 B2 | 9/2014 | Neff et al. | |
| 9,884,427 B2 * | 2/2018 | Low | B25J 17/02 |
| 9,937,626 B2 * | 4/2018 | Rockrohr | B25J 15/0226 |
| 10,390,853 B2 * | 8/2019 | Kapadia | A61B 17/29 |
| 2003/0135204 A1 | 7/2003 | Lee et al. | |
| 2004/0193146 A1 | 9/2004 | Lee et al. | |
| 2005/0165429 A1 | 7/2005 | Douglas et al. | |
| 2005/0240178 A1 | 10/2005 | Morley et al. | |
| 2006/0079890 A1 | 4/2006 | Guerra | |
| 2006/0111735 A1 | 5/2006 | Crainich | |
| 2006/0190034 A1 | 8/2006 | Nishizawa et al. | |
| 2010/0076483 A1 | 3/2010 | Imuta | |
| 2010/0185232 A1 | 7/2010 | Hughett, Sr. et al. | |
| 2010/0191251 A1 | 7/2010 | Scott et al. | |
| 2010/0298638 A1 | 11/2010 | Slater | |
| 2011/0004210 A1 | 1/2011 | Johnson et al. | |
| 2011/0092776 A1 | 4/2011 | Kawai et al. | |
| 2011/0118778 A1 | 5/2011 | Burbank | |
| 2011/0238064 A1 | 9/2011 | Williams | |
| 2011/0251608 A1 | 10/2011 | Timm et al. | |
| 2011/0276049 A1 | 11/2011 | Gerhardt | |
| 2013/0197492 A1 | 8/2013 | Kishi et al. | |

FOREIGN PATENT DOCUMENTS

| | | |
|---|---|---|
| JP | 2006-061364 A | 3/2006 |
| JP | 2008212451 A | 9/2008 |
| WO | 2005072105 A2 | 8/2005 |
| WO | 2013-063675 A1 | 5/2013 |
| WO | 2015-088647 A1 | 6/2015 |

OTHER PUBLICATIONS

Australian Examination Report issued in corresponding Australian Application No. 2016282591 dated Jan. 31, 2020, 3 pages.
First Office Action issued in corresponding Chinese Appl. No. CN201680036200.X dated Mar. 18, 2020, together with English language translation (17 pages).
Japanese Office Action issued in corresponding Japanese Application No. 2017-565928 dated Mar. 25, 2020, 11 pages.

* cited by examiner

SURGICAL END EFFECTORS WITH MECHANICAL ADVANTAGE

CROSS-REFERENCE TO RELATED APPLICATION

This application claims the benefit of and priority to U.S. Provisional Patent Application No. 62/183,383, filed on Jun. 23, 2015, the content of which is incorporated by reference herein in its entirety.

BACKGROUND

Handheld and robotic surgical systems have been used in minimally invasive medical procedures. While handheld systems typically included a handle assembly and an elongated body portion, some robotic surgical systems included a console supporting a robot arm. Nonetheless, both handheld and robotic surgical systems included at least one end effector such as a forceps or a grasping tool that was mounted to the robot arm or the elongated body portion for performing a medical procedure. During a medical procedure, the end effector was inserted into a small incision (via a cannula) or a natural orifice of a patient to position the end effector at a work site within the body of the patient. The end effectors were designed to be moveable through multiple degrees of motion in order to navigate in the work site and/or manipulate tissue therein.

As demand for smaller end effectors increased, device manufacturers continued to develop end effectors such as grasping and cutting end effectors having smaller cross-sectional areas. These smaller cross-sectional areas reduced the total force that could be applied between the jaws of the end effector. However, the need for sufficient mechanical advantage for all end effector configurations, regardless of size and/or motion, continued to factor into end effector design.

Thus, there is a need for end effectors that are able to provide higher forces between two jaws of the end effectors while one or both of the two jaw move between various positions and/or conditions.

SUMMARY

Accordingly, the present disclosure is directed to an end effector that may be adapted for use in manual or robotic surgical systems or instruments. The end effector includes two jaw members and two pulleys that are coupled together to provide mechanical advantage gripping. The two jaw members are indirectly coupled to one another by movable members that rotate and/or translate to enable the two jaw members to move relative to one another for opening and/or closing the two jaw members. Advantageously, the movable members include drive and guide pins coupled to holes and/or slots of the first and second jaw members to effectuate parallel, pivotal, and/or rotational movement of the first and second jaw members relative to one another through various pivot points. While neither of the two jaw members is directly coupled to the other jaw member through a shared pivot point, the two jaw members may define a virtual pivot between the two jaw members to enable rotational movement of the first and second jaw members thereabout.

In one aspect, an end effector includes a first pulley, a second pulley, a pulley pin, a first jaw member, and a second jaw member. The first pulley includes a first drive pin and a first guide pin. The second pulley includes a second drive pin and a second guide pin. The pulley pin is coupled to the first and second pulleys. The first jaw member defines a first hole and a first slot. The first drive pin of the first pulley is received in the first hole of the first jaw member. The second guide pin of the second pulley is received in the first slot of the first jaw member. The second jaw member defines a second hole and a second slot. The first guide pin of the first pulley is received in the second slot of the second jaw member. The second drive pin of the second pulley is received in the second hole of the second jaw member. The first and second jaw members are movable relative to one another between open and closed states in response to rotation of one or both of the first and second pulleys. In some embodiments, the first and second jaw members are positioned to tip-bias toward one another.

In certain embodiments, the first slot of the first jaw member includes a linear portion and a curved portion. The first jaw member may move in parallel relation to the second jaw member as the second guide pin of the second pulley translates through the linear portion of the first slot of the first jaw member. The first jaw member may pivot about the first drive pin of the first pulley and rotate relative to the second jaw member about a virtual pivot defined between the first and second jaw members as the second guide pin of the second pulley translates through the curved portion of the first slot of the first jaw member.

In some embodiments, the first slot of the first jaw member is linear along a length thereof.

In embodiments, the pulley pin extends between the first and second jaw members. The pulley pin may be spaced-apart from the first and second jaw members.

In some embodiments, the second slot of the second jaw member includes a linear portion and a curved portion. The second jaw member may move in parallel relation to the first jaw member as the first guide pin of the first pulley translates through the linear portion of the second jaw member. The second jaw member may pivot about the second drive pin of the second pulley and rotate relative to the first jaw member about a virtual pivot defined between the first and second jaw members as the first guide pin of the first pulley translates through the curved portion of the second slot of the second jaw member.

In embodiments, the second slot of the second jaw member is linear along a length thereof.

According to another aspect, the present disclosure is directed to an end effector for use and connection to a robotic surgical system including one or more connector members extending from a motor of a control device of the robotic surgical system. The end effector includes a first movable member, a second movable member, a first jaw member, and a second jaw member.

The first movable member includes a first drive pin and a first guide pin. The second movable member includes a second drive pin and a second guide pin. The first jaw member defines a first hole and a first slot. The drive pin of the first movable member is received in the first hole of the first jaw member. The second guide pin of the second movable member is received in the first slot of the first jaw member. The second jaw member defines a second hole and a second slot. The first guide pin of the first movable member is received in the second slot of the second jaw member. The second drive pin of the second movable member is received in the second hole of the second jaw member. One or both of the first and second movable members is coupled to the one or more connector members of the robotic surgical system. One or both of the first and second movable members rotates in response to movement of one or both of the first and second movable members to move one or both of the first and second jaw members relative to the other of the first and second jaw members between open and closed states.

In embodiments, the first slot of the first jaw member includes a linear portion and a curved portion to enable bi-modal movement of the first jaw member. The first jaw member may move in parallel relation to the second jaw member as the second guide pin of the second movable member translates through the linear portion of the first slot of the first jaw member.

In some embodiments, the first jaw member may pivot about the first drive pin of the first movable member and rotate relative to the second jaw member about a virtual pivot defined between the first and second jaw members as the second guide pin of the second movable member translates through the curved portion of the first slot of the first jaw member. The first slot of the first jaw member may be linear along a length thereof. The second slot of the second jaw member may include a linear portion and a curved portion. The second jaw member may move in parallel relation to the first jaw member as the first guide pin of the first movable member translates through the linear portion of the second jaw member. The second jaw member may pivot about the second drive pin of the second movable member and rotate relative to the first jaw member about a virtual pivot defined between the first and second jaw members as the first guide pin of the first movable member translates through the curved portion of the second slot of the second jaw member.

In embodiments, the second slot of the second jaw member is linear along a length thereof.

In some embodiments, one or both of the first and second movable members includes first and second links that are axially movable relative to one another to enable the first and second jaw members to move between the open and closed states. In certain embodiments, one or both of the first and second movable members includes a pulley.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1A:
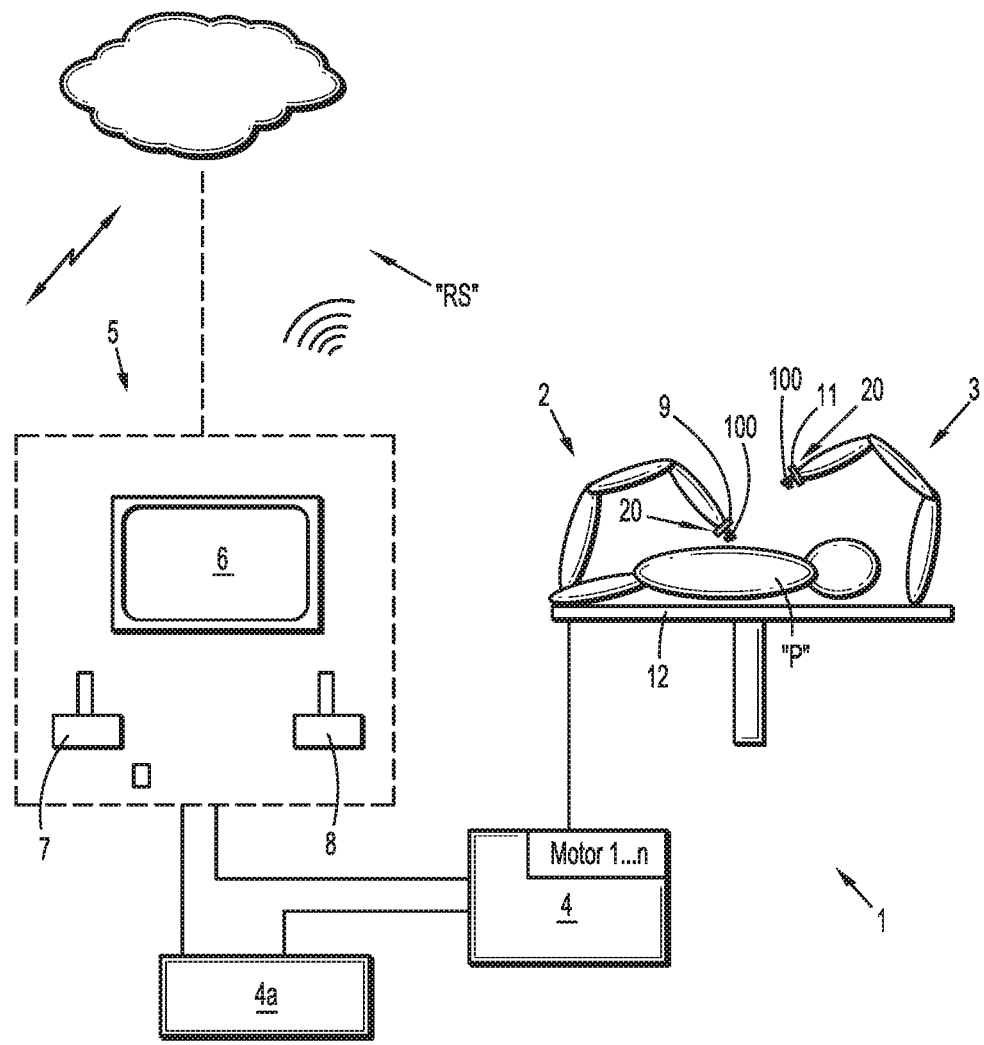
FIG. 1A is a schematic illustration of a robotic surgical system including a medical work station and an operating console in accordance with the present disclosure.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of the device that is closer to the user. As used herein, the term "clinician" refers to a doctor, a nurse or any other care provider and may include support personnel. In the following description, well-known functions or constructions are not described in detail to avoid obscuring the present disclosure in unnecessary detail.

Referring initially to FIG. 1A, a robotic surgical system includes a medical work station 1 and generally includes a plurality of robot arms 2, 3; a controller/control device 4; and an operating console 5 coupled with controller 4. Operating console 5 includes a display device 6, which is set up in particular to display three-dimensional images; and manual input devices 7, 8, by means of which a clinician (not shown), for example a surgeon, is able to telemanipulate robot arms 2, 3 in a first operating mode, as known in principle to a person skilled in the art.

Generally, each of robot arms 2, 3 includes a plurality of members, which are connected through joints, and an attachment device 9, 11, to which may be attached, for example, a surgical tool or surgical instrument 20 supporting an end effector 100.

Robot arms 2, 3 may be driven by one or more electric drives or motors operatively connected to control device 4. Control device 4 may include a computer and is set up to activate the motors, in particular by means of a computer program, in such a way that robot arms 2, 3, their attachment devices 9, 11 and/or the surgical tool 20 (including end effector 100) execute a desired movement according to a movement defined by manual input devices 7, 8.

Figure 1B:
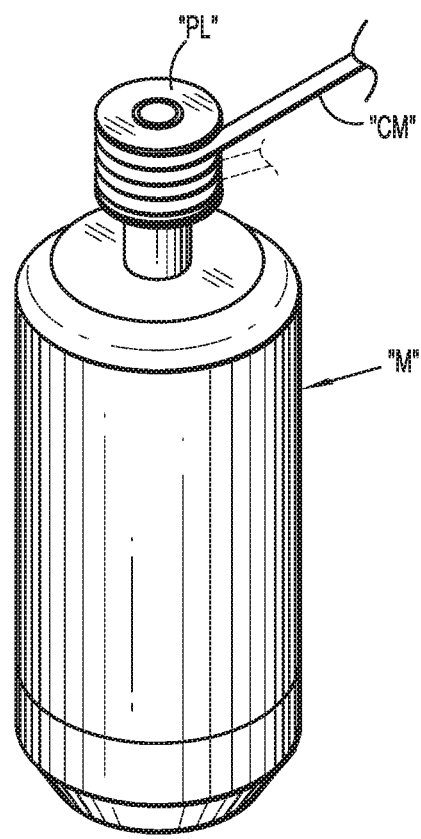
FIG. 1B is a schematic, perspective view of a motor of a control device of the medical work station of FIG. 1A.

With reference also to FIG. 1B, control device 4 may control a plurality of motors "M" (Motor 1 . . . n) with each motor configured to wind-up and/or let out a length of a connector member "CM" (e.g., cables, chains, belts, rods, etc., and/or combinations thereof) extending through each robot arm 2, 3 to end effector 100 of surgical tool 20 (FIG. 1A). For example, one or more connector members "CM" can be coupled directly and/or indirectly between one or more pulleys "PL" associated with one or more of motors "M" and one or more pulleys (see e.g., FIGS. 2, 3, and/or 5) associated with end effector 100. In use, as connector members "CM" are wound-up and/or let out, connector members "CM" effect operation and/or movement of each end effector 100 of surgical tool 20. Control device 4 coordinates the activation of the various motors "M" to coordinate a winding-up and/or letting out a length of a respective connector member "CM" in order to coordinate an operation and/or movement of a respective end effector 100. In some instances, a single connector member "CM" is wound up and/or let out by a single motor. However, in certain instances, two or more connector members or two ends of a single connector member may be wound up and/or let out by a single motor. For example, two connector members or connector member ends may be coupled in opposite directions to a single motor so that as motor "M" is activated in a first direction, one of the connector members winds up while the other connector members lets out. Other connector member configurations may be used in different embodiments.

Control device 4 can include any suitable logic control circuit adapted to perform calculations and/or operate according to a set of instructions. Control device 4 can be configured to communicate with a remote system "RS," wirelessly (e.g., Wi-Fi, Bluetooth, LTE, etc.) and/or wired. Remote system "RS" can include data, instructions and/or information related to the various components, algorithms, and/or operations of work station 1. Remote system "RS" can include any suitable electronic service, database, platform, cloud, or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include one or more counters to count, for example, a number of uses of one or more of the components of the medical work station (e.g., connector members "CM," end effector 100, etc.). Controller 4 can include a plurality of inputs and outputs for interfacing with the components of work station 1, such as through a driver circuit. Controller 4 can be configured to receive input signals and/or generate output signals to control one or more of the various components (e.g., one or more motors 16) of work station 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to remote system "RS."

A database 4a can be directly and/or indirectly coupled to control device 4. Database 4a can be configured to store pre-operative data from living beings or patients "P" and/or anatomical atlases. Database 4a can include memory, which can be part of, and/or or operatively coupled to, remote system "RS."

Work station 1 is configured for use on a patient "P" lying on a patient table 12 to be treated in a minimally invasive manner by means of end effector 100. Work station 1 may also include more than two robot arms 2, 3, the additional robot arms likewise being connected to controller 4 and being telemanipulatable by means of operating console 5. One or more surgical instruments 20 may be attached to the additional robot arms.

Reference may be made to U.S. Patent Publication No. 2012/0116416, filed on Nov. 3, 2011, entitled "Medical Workstation," the entire contents of which are incorporated herein by reference, for a detailed discussion of the construction and operation of work station 1.

Figure 1C:
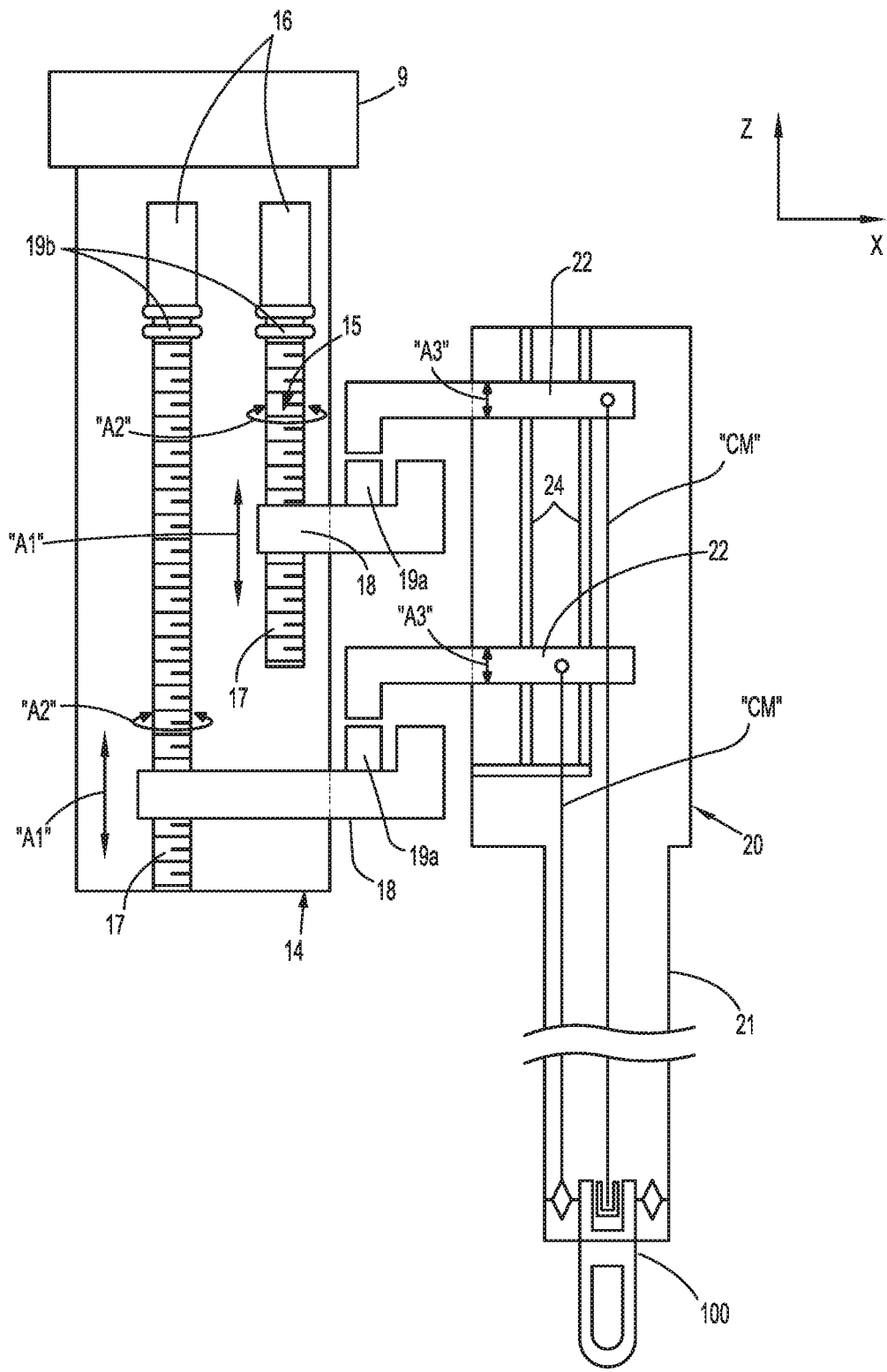
FIG. 1C is a schematic view of a drive unit and an attachment device coupled to a robot arm of the medical work station of FIG. 1A.

FIG. 1C shows an exemplary attachment device 9 having a drive unit 14 coupled thereto. Drive unit 14 and/or attachment device 9 may be directly and/or indirectly attached to, and/or integrally formed with, one of robot arms 2, 3. For example, in some instances, drive unit 14 is directly attached to one of robot arms 2, 3 and attachment device 9 is indirectly attached to one of robot arm 2, 3 while attachment device 9 is coupled to drive unit 14. In certain instances, attachment device 9 is directly attached to one of the robot arms 2, 3 and drive unit 14 is indirectly attached to robot arm 2, 3 while drive unit 14 is coupled to attachment device 9. In some instances, both attachment device 9 and drive unit 14 are directly attached to one of robot arms 2, 3.

Drive unit 14 includes a drive assembly 15 having one or more motors 16 and one or more drive members 17 coupled to the one or more motors 16. Motor 16 is electrically coupled to controller 4 and operable to impart movement (e.g., rotational movement) to drive member 17. In some embodiments, drive member 17 is a lead screw. One or more drive tabs 18 are mounted to each drive member 17 and movable there along. As illustrated by arrows "A1," drive tab 18 is movable relative to drive member 17 in an axial direction (e.g., along the z-axis) in response to rotational movement of drive member 17 in clockwise and/or counterclockwise directions as illustrated by arrows "A2." In some embodiments, drive tab 18 is a split nut drive tab.

Drive tab 18 may be threadably coupled to drive member 17 to effectuate movement of drive tab 18 relative to drive member 17. Drive tab 18 and/or drive member 17 may include any suitable threading configuration. For example, one or more of the threads of drive tab 18 and/or drive member 17 can have any suitable shape, diameter, pitch, direction/orientation, etc. In some embodiments, drive member 17 may include multiple sets of threads, each set of threads being threaded in an opposite direction as compared to an adjacent set of threads. In certain embodiments, each set of threads is configured to engage a different drive tab 18 to impart approximating and/or unapproximating movement between multiple drive tabs 18.

Drive tab 18 includes a force sensor 19a (e.g., a transducer or the like) operatively coupled to controller 4 and configured to determine applied force. Drive member 17 supports a position sensor 19b operatively coupled to controller 4 and configured to determine one or more positions of one or more components (e.g., drive tab 18) of drive assembly 15 relative to other components thereof (e.g., drive member 17). For example, position sensor 19b is configured to measure a position and/or movement of an output of motor 16, drive member 17, and/or drive tab 18.

As seen in the exemplary embodiment shown in FIG. 1C, drive unit 14 couples to surgical tool 20 (see FIG. 1A) or instrument such as surgical instrument 20. Surgical instrument 20 includes one or more instrument tabs 22 movably mounted on one or more supports or rails 24. For example, instrument tab 22 can be axially movable along rails 24 in the z-direction as indicated by arrows "A3." One or more connector members "CM" are coupled to instrument tabs 22 and extend along a shaft assembly 21 of surgical instrument 20 to end effector 100 thereof for effectuating movement of end effector 100 and/or portions thereof in response to movement of the one or more connector members "CM." As described above with respect to FIG. 1B, connector members "CM" may include cables, chains, rods, belts, etc., and/or combinations thereof. Additionally, and/or alternatively, connector members "CM" can be moved for imparting forces to end effector 100, for example, to fire end effector (e.g., staples, clips, etc.).

Control device 4 may control current applied to motor 16 during a surgical procedure. The current supplied to motor 16 may be adjusted to move drive member 17 and drive tab 18 so that drive tab 18 pushes against and moves a corresponding instrument tab 22 of surgical instrument 20 in the same z-direction to move a component of surgical instrument 20 such as end effector 100 via one or more connector members "CM." In the example shown in FIG. 1C, each connector member "CM" in surgical instrument 20 is attached at one end to a respective instrument tab 22 and at an opposite end to a respective portion of end effector 100. Each connector member "CM" is connected to a different portion of end effector 100 in order to cause different movements of the end effector 100 (e.g., articulation, rotation, open/close jaw members thereof, etc.) in response to movement of respective instrument tabs 22 via corresponding drive tabs 18 and/or motors 16 of drive unit 14.

Figure 2:
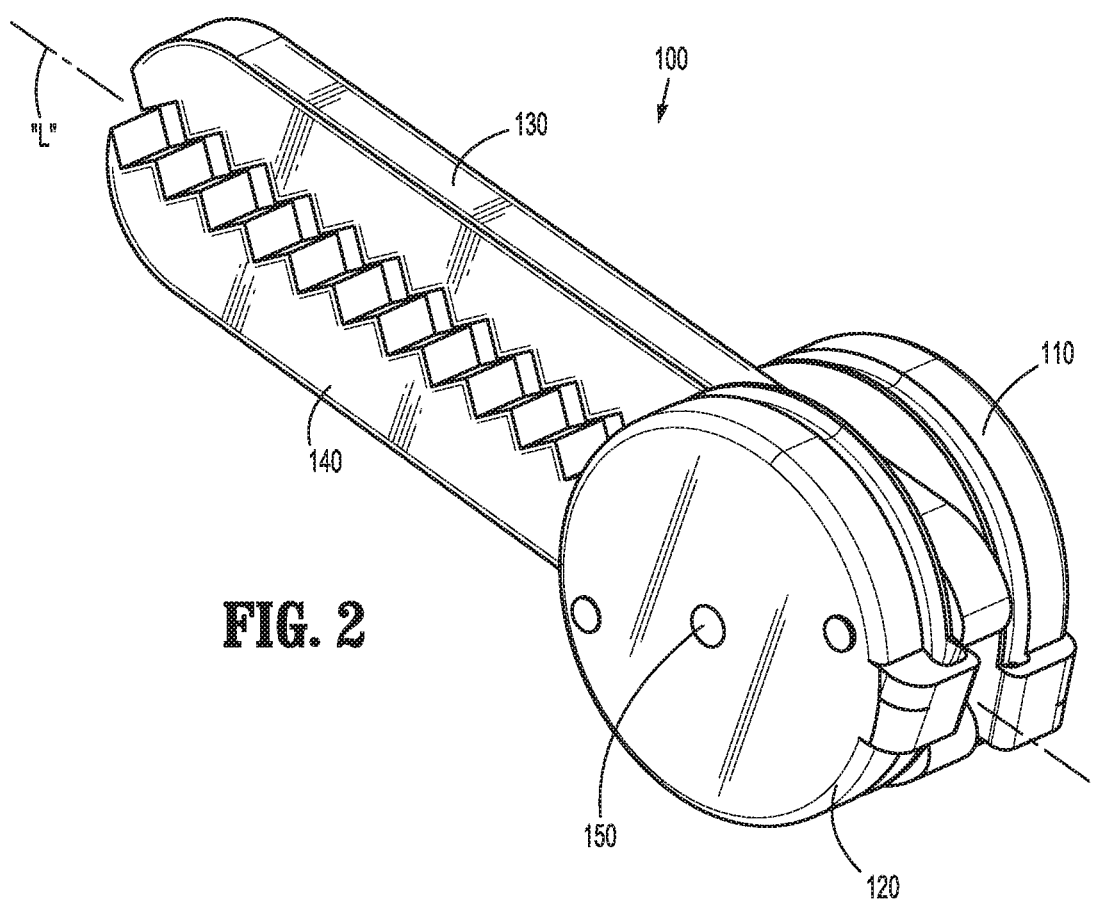
FIGS. 2 and 3 are perspective views of an end effector, according to an exemplary embodiment of the present disclosure, for use in the medical work station of FIG. 1A.
Figure 3:
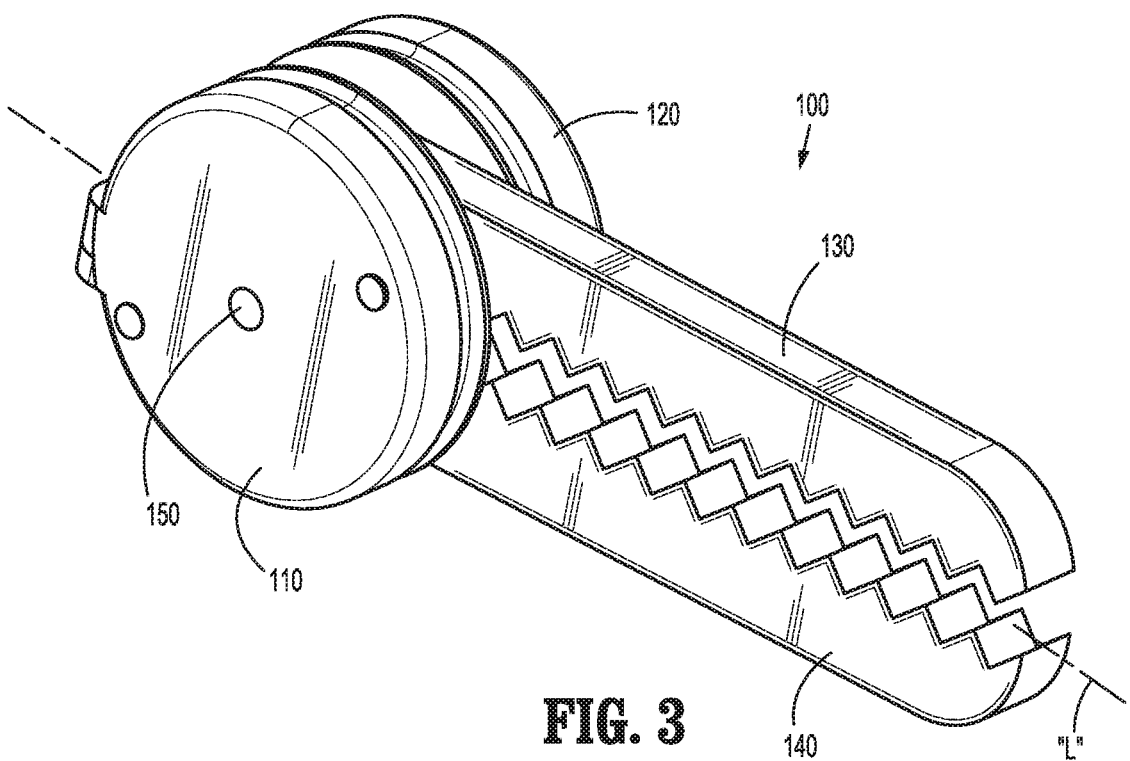

Turning now to FIGS. 2 and 3, end effector 100 defines a central longitudinal axis "L" that extends through proximal and distal ends of end effector 100. End effector 100 includes a first movable member or pulley 110, a second movable member or pulley 120, a first jaw member 130, a second jaw member 140, and a connector pin 150.

Figure 4:
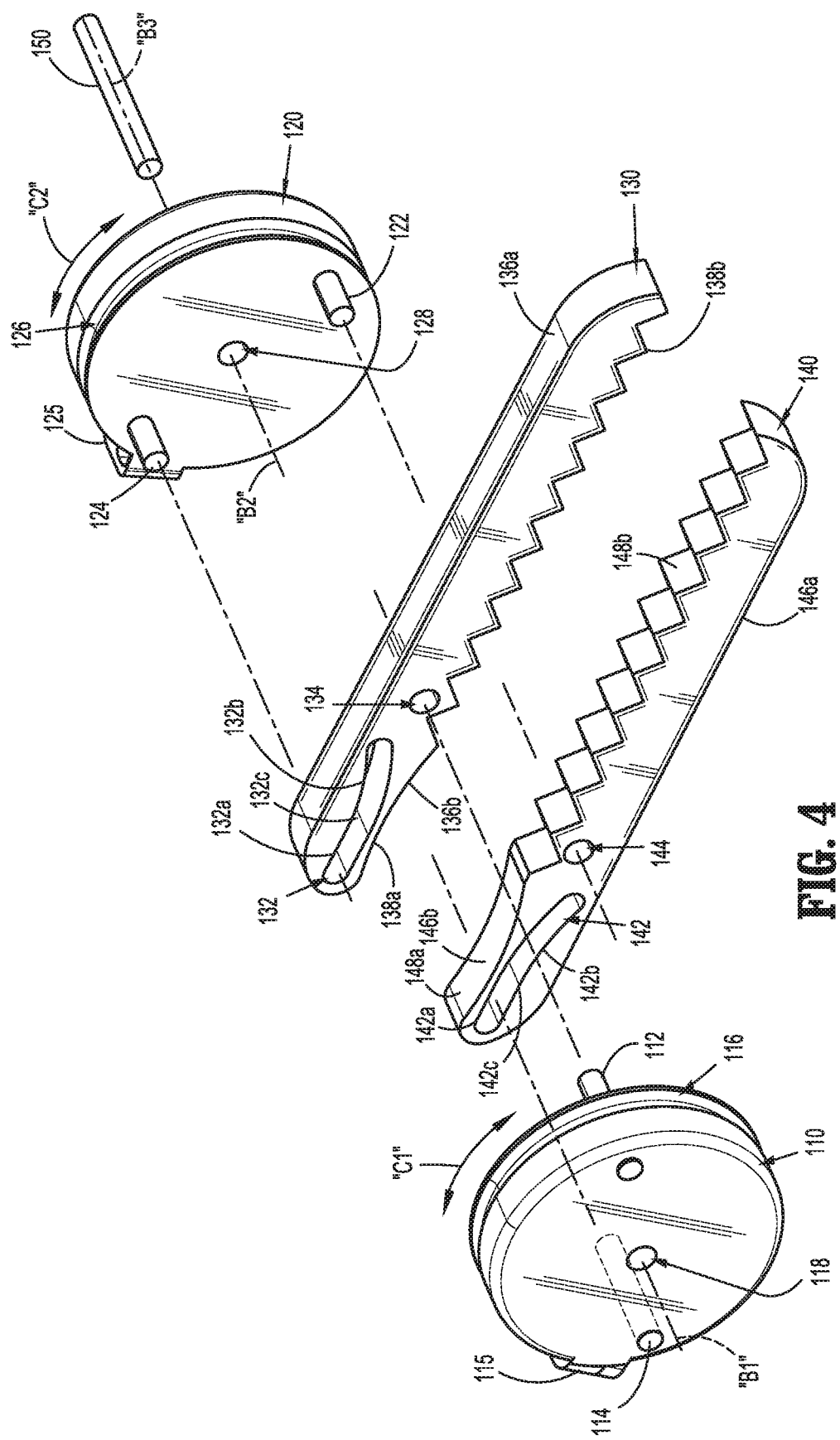
FIG. 4 is a perspective view, with parts separated, of the end effector of FIGS. 2 and 3.
Figure 5:
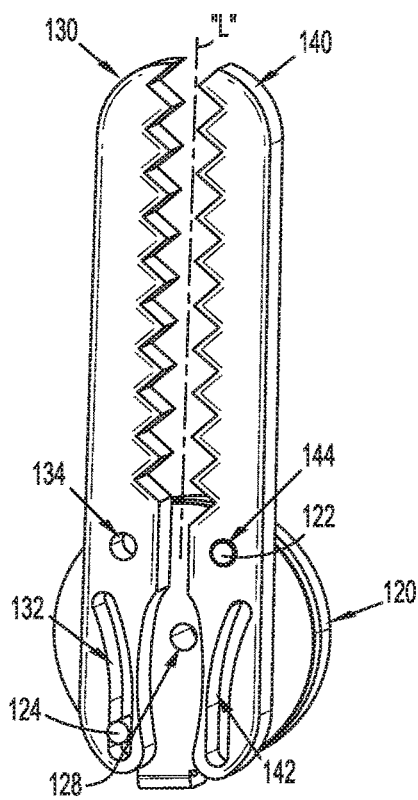
FIG. 5 is a perspective, side view of the end effector of FIGS. 2 and 3 with a pulley thereof removed for clarity.

With reference to FIGS. 4 and 5, first pulley 110 includes a first drive pin 112 and a first guide pin 114 extending therefrom. A mounting member 115 also extends from first pulley 110. First pulley 110 defines a channel 116 in an outer surface thereof and a pulley pin opening 118 therethrough. First pulley 110 couples to one or more connector members "CM" of work station 1 (see FIGS. 1A to 1C) to enable first pulley 110 to rotate about a first axis of rotation "B1" as indicated by arrow "C1."

Second pulley 120 mirrors first pulley 110 and includes a second drive pin 122 and a second guide pin 124 extending therefrom. A mounting member 125 also extends from second pulley 120. Second pulley 120 defines a channel 126 in an outer surface thereof and a pulley pin opening 128 therethrough. Like first pulley 110, second pulley 120 couples to a connector member "CM" of work station 1 (see FIGS. 1A to 1C) to enable second pulley 120 to rotate about a second axis of rotation "B2" as indicated by arrow "C2."

First jaw member 130 defines a first slot 132 having a linear portion 132a at a proximal end thereof and a curved portion 132b at a distal end thereof. Linear portion 132a and curved portion 132b are separated by an inflection point 132c. First slot 132 receives second guide pin 124 of second pulley 120. As described in greater detail below, second guide pin 124 is movable through first slot 132 such that first jaw member 130 is disposed at an angled orientation relative to central longitudinal axis "L" of end effector 100 while second guide pin 124 is positioned at a distal end of first slot 132, and disposed in a parallel orientation relative to central longitudinal axis "L" while second guide pin 124 is positioned at a proximal end of first slot 132. First jaw member 130 further defines a first hole 134 that receives first drive pin 112 of first pulley 110. First jaw member 130 includes an outer surface 136a and an inner surface 136b. Inner surface 136b of first jaw member 130 includes a recessed portion 138a at a proximal end thereof and a tissue contact surface 138b at a distal end thereof.

Second jaw member 140 mirrors first jaw member 130 and defines a second slot 142 having a linear portion 142a at a proximal end thereof and a curved portion 142b at a distal end thereof. Linear portion 142a and curved portion 142b are separated by an inflection point 142c. Second slot 142 receives first guide pin 114 of first pulley 110. As described in greater detail below, first guide pin 114 is movable through second slot 142 such that second jaw member 140 is disposed at an angled orientation relative to central longitudinal axis "L" of end effector 100 while first guide pin 114 is positioned at a distal end of second slot 142 of second jaw member 140, and disposed in a parallel orientation relative to central longitudinal axis "L" while first guide pin 114 is positioned at a proximal end of second slot 142 of second jaw member 140. Second jaw member 140 further defines a second hole 144 that receives second drive pin 122 of second pulley 120. Second jaw member 140 includes an outer surface 146a and an inner surface 146b. Inner surface 146b of second jaw member 140 includes a recessed portion 148a at a proximal end thereof and a tissue contact surface 148b at a distal end thereof.

Connector pin 150 defines a central axis "B3" therethrough and couples first and second pulleys 110, 120 together while secured within pulley pin opening 118 of first pulley 110 and second pulley pin opening 128 of second pulley 120. First and second jaw members 130, 140 are secured between first and second pulleys 110, 120 while first and second pulleys 110, 120 are secured together by connector pin 150. Central axis "B3" of connector pin 150 is coincident with first and second axes of rotation "B1" and "B2" of first and second pulleys 110, 120 while connector pin 150 is received within pulley pin openings 118, 128 of first and second pulleys 110, 120.

In use, one or both of first and second pulleys 110, 120 are rotated (e.g., clockwise and/or counterclockwise) about connector pin 150, as indicated by arrows "C1" and "C2" (FIG. 4) in response to movement of one or more connector members "CM" (see, e.g., FIGS. 1B and/or 1C). Pulley rotation causes first guide pin 114 of first pulley 110 to translate through second slot 142 of second jaw member 140, and second guide pin 124 of second pulley 120 to translate through first slot 132 of first jaw member 130. As seen in FIGS. 6 to 9, rotation of one or both of first and second pulleys 110, 120 enables first and second jaw members 130, 140 to move between open (see, e.g., FIG. 6) and closed states (see, e.g., FIG. 9) relative to one another.

Figure 7:
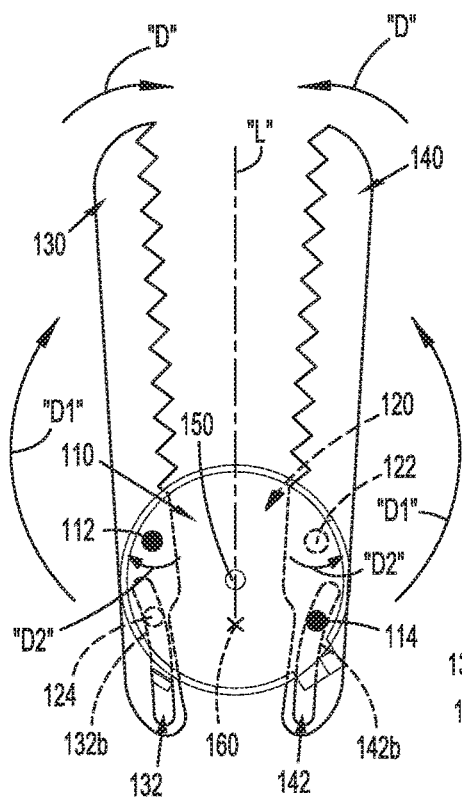
Figure 8:
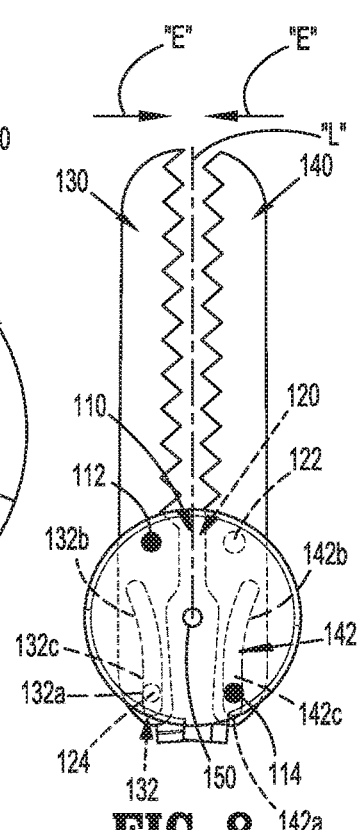

Movement of first and second jaw members 130, 140 between the open and closed states is bi-modal (e.g., multi-axial motion which can include both arcuate and/or parallel motion of the first and/or second jaw members 130, 140) (see FIG. 6) and includes a first mode in which first and second jaw members 130, 140 move angularly, as indicated generally by arrows "D" (FIGS. 6 and 7), and a second mode in which first and second jaw members 130, 140 move in parallel relation to one another, as indicated generally by arrows "E" (FIG. 8). Angular movement of first and second jaw members 130, 140 in the first mode corresponds to translation of guide pins 114, 124 of respective first and second pulleys 110, 120 through curved portions 132b, 142b of guide slots 132, 142 of respective first and second jaw members 130, 140. Parallel movement of first and second jaw members 130, 140 in the second mode corresponds to translation of guide pins 114, 124 of respective first and second pulleys 110, 120 through linear portions 132a, 142a of guide slots 132, 142 of respective first and second jaw members 130, 140. Transition between the angular and parallel movement of first and second jaw members 130, 140 occurs as guide pins 114, 124 of respective first and second pulleys 110, 120 crosses inflection points 132c, 142c of slots 132, 142 of respective first and second jaw members 130, 140.

Figure 6:
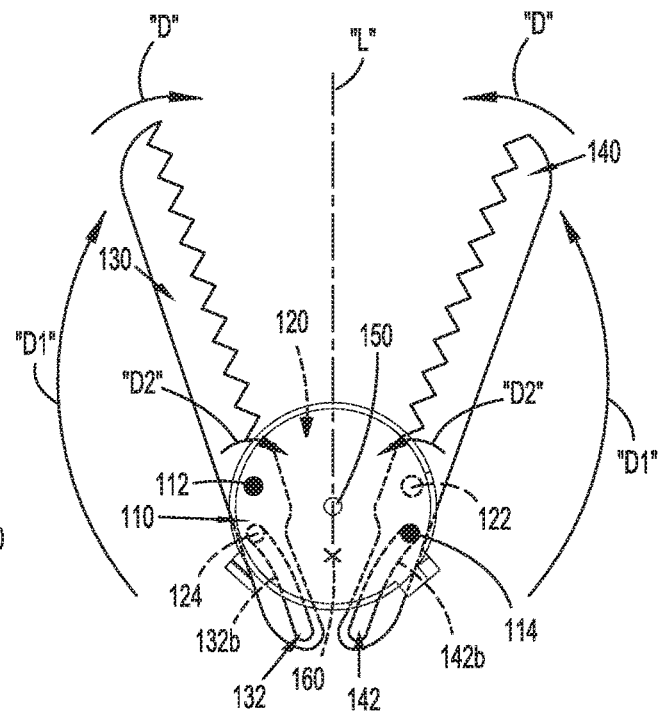
FIGS. 6 to 9 are progressive side views of the end effector of FIGS. 2 and 3 showing movement of the end effector between open and closed states.

In the first mode of the two modes of jaw member movement, angular movement of one or both of first and second jaw members 130, 140 provides two degrees of movement, namely, pivoting and/or rotating movement of first and/or second jaw members 130, 140 relative to one another. With reference to FIGS. 6 and 7, in a first degree of movement of the two degrees of movement in the first mode, as indicated by arrows "D1," first and second jaw members 130, 140 rotate relative to one another about a virtual pivot point/axis generally referred to as virtual pivot 160 defined between first and second jaw members 130, 140.

Virtual pivot 160 is defined by a configuration of first and second guide slots 132, 142 of first and second jaw members 130, 140, respectively, as well as a configuration of first and second guide pins 114, 124 of first and second pulleys 110, 120, respectively, with the location of the virtual pivot 160 configured to change depending on such configurations. Virtual pivot 160 may have any suitable location in that first and second guide slots 132, 142 of respective first and second jaw members 130, 140, as well as first and second guide pins 114, 124 of respective first and second pulleys 110, 120 can include any suitable configuration (e.g., shape, dimension, and/or position relative to one or more other components of end effector 100).

With continued reference to FIGS. 6 and 7, in a second degree of movement of the two degrees of movement in the first mode, arrows "D2" indicate pivoting movement of first and second jaw members 130, 140 about respective drive pins 114, 124. The pivoting movement of one or both of first and second jaw members 130, 140 may be concurrent, successive, and/or otherwise patterned with the rotating movement of one or both of the first and second jaw members 130, 140. An amount of pivoting and/or rotating movement may depend on orientation, position, and/or state of one or both of first and second jaw members 130, 140.

Figure 9:
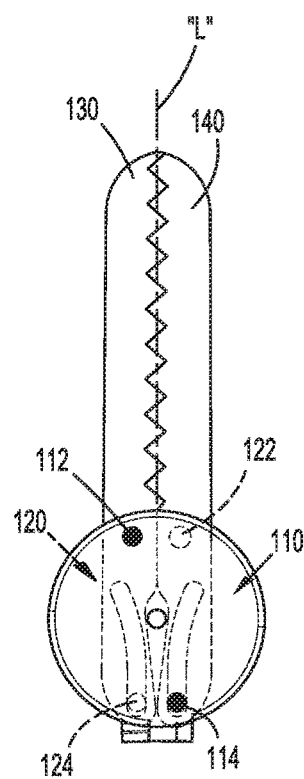
Figure 10:
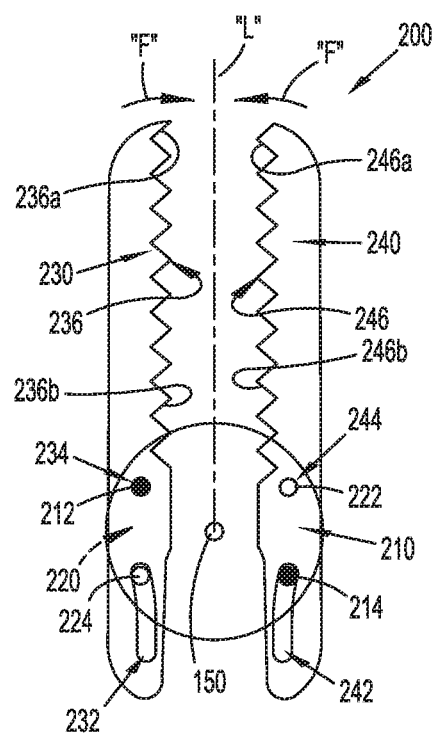
FIGS. 10 to 13 are progressive side views of another exemplary embodiment of an end effector in accordance with the present disclosure.
Figure 11:
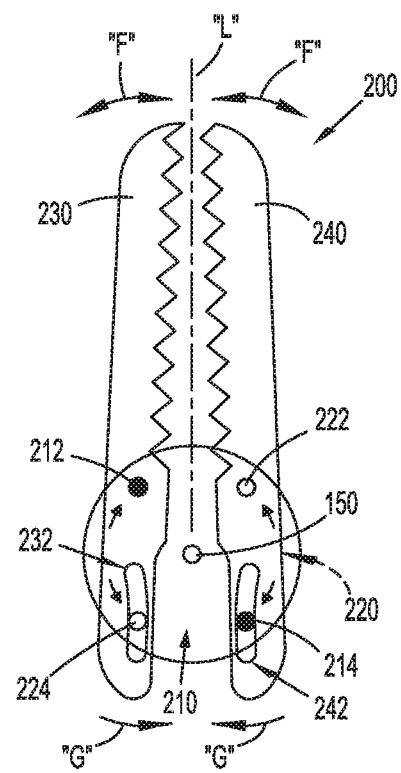
Figure 12:
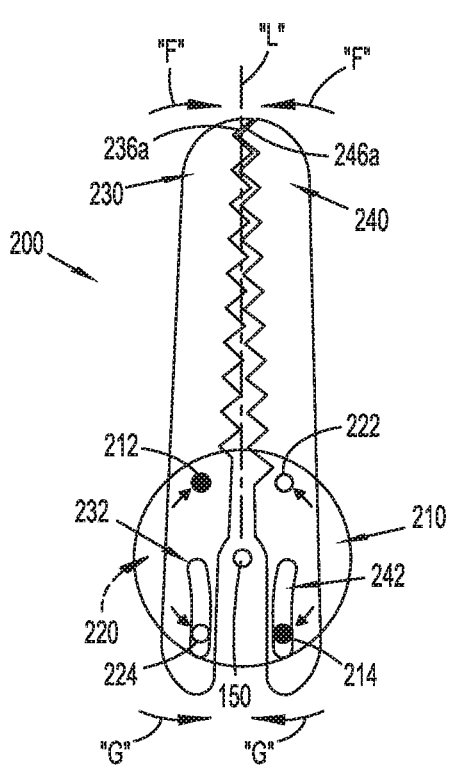
Figure 13:
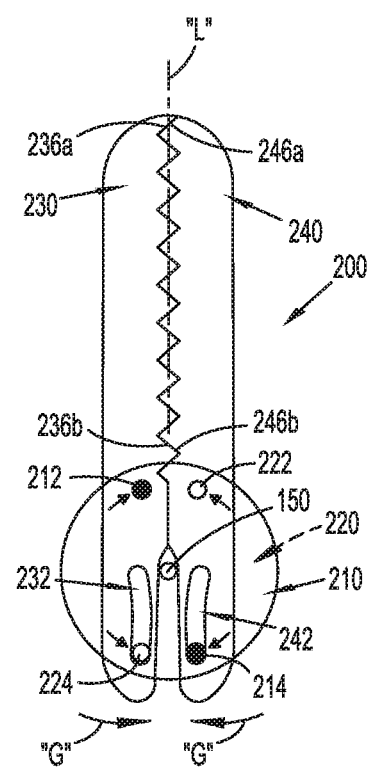
Figure 14:
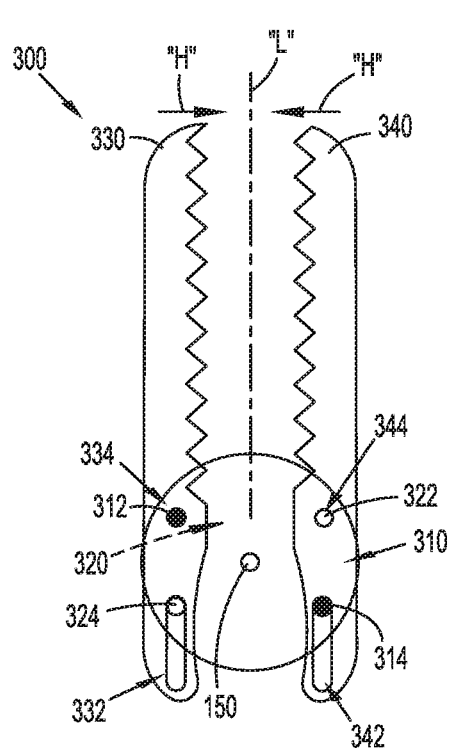
FIGS. 14 to 17 are progressive side views of yet another exemplary embodiment of an end effector in accordance with the present disclosure.
Figure 15:
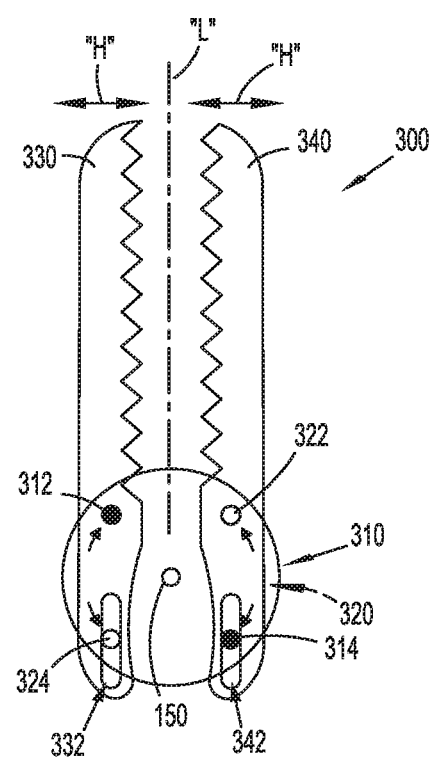
Figure 16:
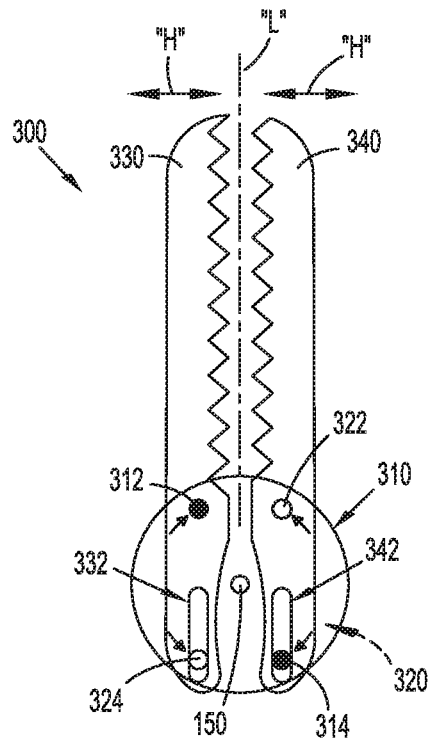
Figure 17:
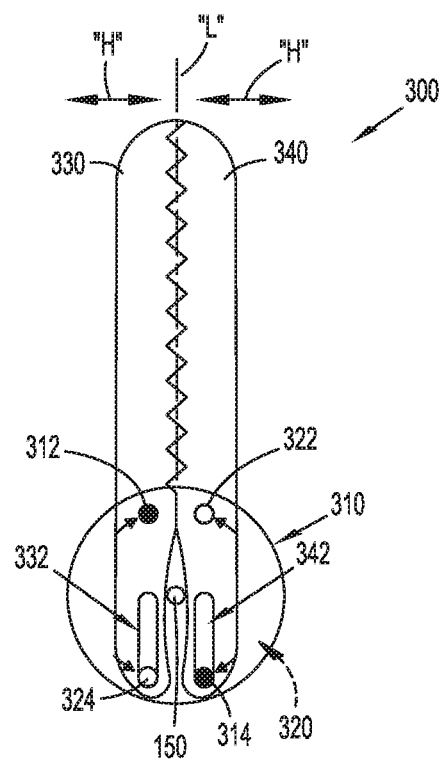

With reference to FIGS. 8 and 9, in the second mode of the two modes of jaw member movement, relative parallel movement between first and second jaw members 130, 140, which provides a single degree of movement, enables tissue contact surfaces 138b, 148b of first and second jaw members 130, 140 to provide even pressure along a length of respective tissue contact surfaces 138b, 148b to tissue (not shown) grasped between first and second jaw members 130, 140.

Turning now to FIGS. 10 to 13, another embodiment of an end effector, generally referred to as end effector 200 is provided. End effector 200 is substantially similar to end effector 100 and is only described herein to the extent necessary to describe the differences in construction and operation of end effector 200 with respect to end effector 100. End effector 200 includes a first movable member or pulley 210, a second movable member or pulley 220, a first jaw member 230, a second jaw member 240, and a connector pin 150.

Connector pin 150 couples first and second jaw members 230, 240 to first and second movable members 210, 220. First movable member 210 includes a first drive pin 212 and a first guide pin 214 that extend therefrom and second movable member 220 includes a second drive pin 222 and a second guide pin 224 that extend therefrom. First jaw member 230 defines a first slot 232 and a first hole 234, and second jaw member 240 defines a second slot 242 and a second hole 244.

In use, first and second movable members 210, 220 are rotated (e.g., upon an actuation of one or more connector members "CM" as described above; see FIGS. 1B and/or 1C) in clockwise and/or counterclockwise directions. As first and second movable members 210, 220 rotate, respective drive and guide pins 212, 214, 222, 224 of first and second movable members 210, 220 and respective slots and holes 232, 234, 242, 244 of first and second jaw members 230, 240 are arranged such that first and second jaw members 230, 240 move between open and closed states. In the open state (FIG. 10), first and second jaw members 230, 240 are disposed in parallel relation relative to one another and to a central longitudinal axis "L" of end effector 200. As indicated by arrows "F" and "G," when first and second jaw members 230, 240 move toward the closed state (FIG. 13), first and second jaw members 230, 240 tip-bias such that distal ends 236a, 246a of tissue contact surfaces 236, 246 of respective first and second jaw members 230, 240 contact each other before proximal ends 236b, 246b of first and second jaw members 230, 240 contact each other.

Turning now to FIGS. 14 to 17, another embodiment of an end effector, generally referred to as end effector 300, is provided. End effector 300 is substantially similar to end effectors 100, 200 and is only described herein to the extent necessary to describe the differences in construction and operation of end effector 300 with respect to end effectors 100, 200. End effector 300 includes a first movable member or pulley 310, a second movable member or pulley 320, a first jaw member 330, a second jaw member 340, and a connector pin 150.

Connector pin 150 couples first and second jaw members 330, 340 to first and second movable members 310, 320. First movable member 310 includes a first drive pin 312 and a first guide pin 314 that extend therefrom, and second movable member 320 includes a second drive pin 322 and a second guide pin 324 that extend therefrom. First jaw member 330 defines a first slot 332 and a first hole 334 and second jaw member 340 defines a second slot 342 and a second hole 344. Slots 332, 342 of respective first and second jaw members 330, 340 extend linearly from a proximal end thereof to a distal end thereof to enable continuous parallel movement of first and second jaw members 330, 340 relative to one another and to a central longitudinal axis "L" of end effector 300.

In use, first and second movable members 310, 320 are rotated about connector pin 150 (e.g., upon an actuation of one or more connector members "CM" as described above; see FIGS. 1B and/or 1C) in clockwise and/or counterclockwise directions. Rotation of first and second movable members 310, 320 about connector pin 150 moves first and second jaw members 330, 340 in parallel relation to one another as first and second jaw members 330, 340 move between open and closed states. As indicated by arrows "H," first and second jaw members 330, 340 maintain continuous parallel relation with one another and with central longitudinal axis "L" of end effector 300.

Figure 18:
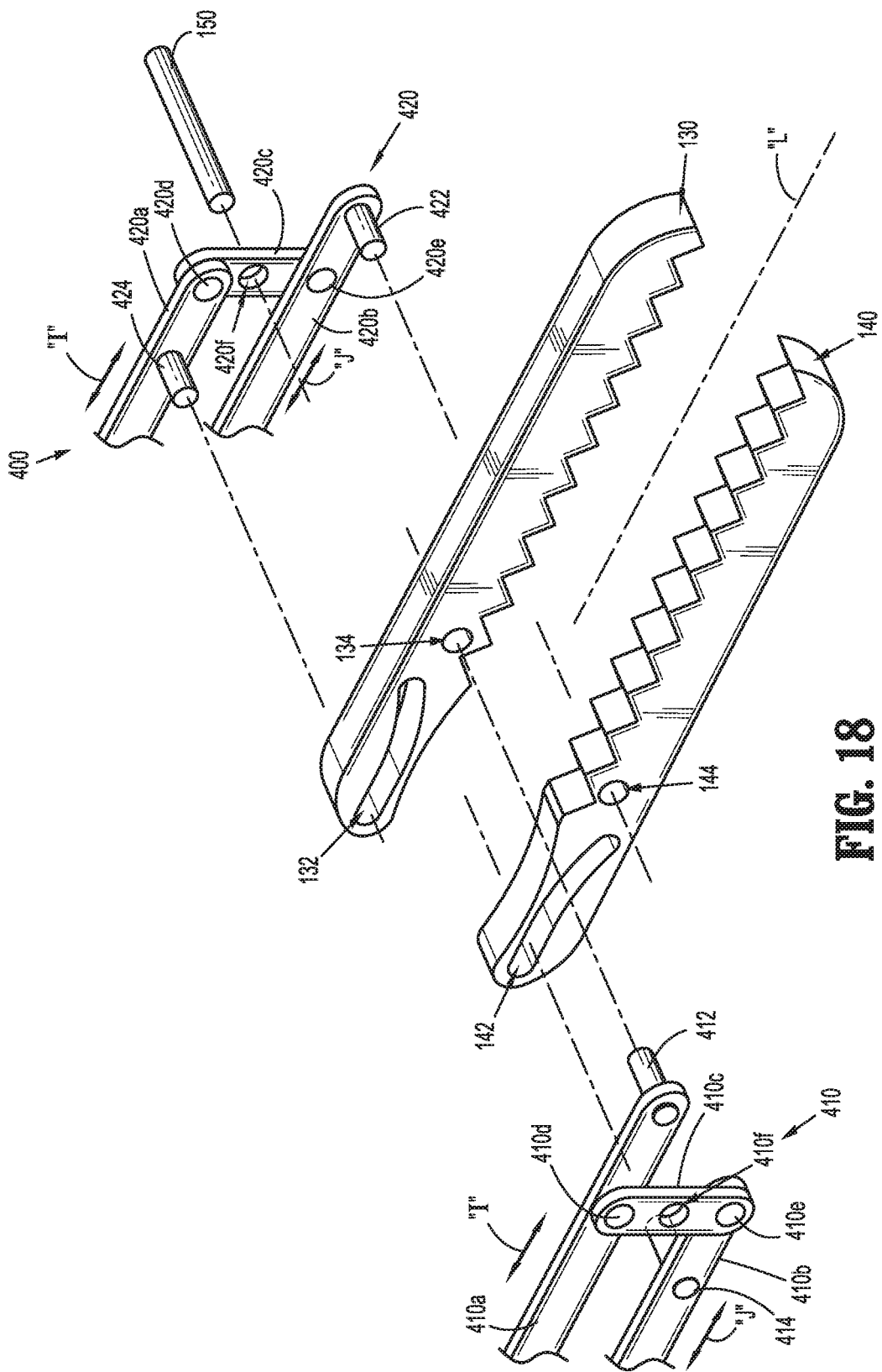
FIG. 18 is a perspective view, with parts separated, of still another exemplary embodiment of an end effector in accordance with the present disclosure.

Turning now to FIG. 18, still another embodiment of an end effector, generally referred to as end effector 400, is provided. End effector 400 is substantially similar to end effectors 100, 200, 300 and is only described herein to the extent necessary to describe the differences in construction and operation of end effector 400 with respect to end effectors 100, 200, 300. End effector 400 includes a first movable member 410, a second movable member 420, a first jaw member 130, a second jaw member 140, and a connector pin 150.

First movable member 410 includes a first drive link 410a, a first guide link 410b, and a first pivot link 410c. First drive and guide links 410a, 410b are pivotally connected to first pivot link 410c by first pivot pins 410e, 410d. First drive link 410a includes a first drive pin 412 extending therefrom and first guide link 410b includes a first guide pin 414 extending therefrom. First pivot link 410c defines a first opening 410f therethrough that receives connector pin 150.

Second movable member 420 is similar to first movable member 410 and includes a second guide link 420a, a second drive link 420b, and a second pivot link 420c. Second guide and drive links 420a, 420b of second movable member 420 are pivotally connected to second pivot link 420c of second movable member 420 by second pivot pins 420e, 420d. Second guide link 420a of second movable member 420 includes a second guide pin 424 extending therefrom. Second drive link 420b of second movable member 420 includes a second drive pin 422 extending therefrom. Second pivot link 420c of second movable member 420 defines a second opening 420f therethrough that receives connector pin 150.

As described above with respect to end effector 100, first and second jaw members 130, 140 define slots 132, 142 and holes 134, 144, respectively. First slot 132 of first jaw member 130 receives second guide pin 424 of second movable member 420 and second slot 142 of second jaw member 140 receives first guide pin 414 of first movable member 410. First hole 134 of first jaw member 130 receives first drive pin 412 of first movable member 410 and second hole 144 of second jaw member 140 receives second drive pin 422 of second movable member 420.

In use, first and second guide and drive links 410a, 410b, 420a, 420b of respective first and second movable members 410, 420 function as, and/or may be connected to, one or more connector members "CM" (see, e.g., FIGS. 1B and/or 1C). As indicated by arrows "I" and "J," first and second guide and drive links 410a, 410b, 420a, 420b of respective first and second movable members 410, 420 are axially movable to move first and second jaw members 130, 140 as described above with respect to end effector 100. In embodiments, first and second jaw members 130, 140 can be replaced with first and second jaw members 230, 240 and/or first and second jaw members 330, 340 such that axial movement of first and second guide and drive links 410a, 410b, 420a, 420b of respective first and second movable members 410, 420 effectuates tip-biasing and/or relative parallel movement as described above with respect to end effectors 200, 300.

Briefly, first and second guide and drive pins 412, 414, 422, 424 of respective first and second movable members 410, 420 move respective first and second jaw members 430, 440 between open and closed states as first and second guide and drive links 410a, 410b, 420a, 420b of respective first and second movable members 410, 420 are axially translated relative to one another. While first drive link 410a of first movable member 410 axially translates in a proximal direction, first guide link 410b of first movable member 410 translates in a distal direction, and vice versa. Similarly, while second guide link 420a of second movable member 420 translates in a proximal direction, second drive link 420b of second movable member 420 translates in a distal direction, and vice versa.

In embodiments, first and second jaw members 130, 140 can be replaced with first and second jaw members 230, 240, and/or first and second jaw members 330, 340. For example, first and second jaw members 130, 140 of end effector 400 may be replaced with first and second jaw members 230, 240, 330, and/or 340 such that axial movement of first and second guide and drive links 410a, 410b, 420a, 420b of respective first and second movable members 410, 420 effectuates tip-biasing and/or relative parallel movement as described above with respect to end effectors 200, 300.

While the presently disclosed end effectors are generally described in a closing context, opening of any of the presently described end effectors can be achieved by reversing direction of motion of one or more of the above described components.

Although embodiments of the presently disclosed end effectors are described herein with respect to robotic surgical instruments, the end effectors described herein can be used and/or modified for use in connection with any suitable handheld instrument such as a surgical grasper or scissor, including tissue cutting and holding devices where electrical, RF, microwave, and/or ultrasound energy is applied.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. An end effector, comprising:
   a first pulley including a first drive pin and a first guide pin;
   a second pulley including a second drive pin and a second guide pin;
   a first jaw member defining a first hole and a first slot, the first drive pin of the first pulley received in the first hole of the first jaw member, the second guide pin of the second pulley received in the first slot of the first jaw member;
   a second jaw member defining a second hole and a second slot, the first guide pin of the first pulley received in the second slot of the second jaw member, the second drive pin of the second pulley received in the second hole of the second jaw member,
   wherein the first and second jaw members are movable relative to one another between open and closed states in response to rotation of at least one of the first and second pulleys; and
   a connector pin pivotally coupling the first and second pulleys.

2. The end effector of claim 1, wherein the first slot of the first jaw member includes a linear portion and a curved portion.

3. The end effector of claim 2, wherein the first jaw member moves in parallel relation to the second jaw member as the second guide pin of the second pulley translates through the linear portion of the first slot of the first jaw member.

4. The end effector of claim 2, wherein the first jaw member pivots about the first drive pin of the first pulley and rotates about a virtual pivot defined between the first and second jaw members as the second guide pin of the second pulley translates through the curved portion of the first slot of the first jaw member.

5. The end effector of claim 2, wherein the second slot of the second jaw member includes a linear portion and a curved portion.

6. The end effector of claim 5, wherein the second jaw member moves in parallel relation to the first jaw member as the guide pin of the first pulley translates through the linear portion of the second jaw member.

7. The end effector of claim 6, wherein the second jaw member pivots about the second drive pin of the second pulley and rotates about a virtual pivot defined between the first and second jaw members as the first guide pin of the first pulley translates through the curved portion of the second slot of the second jaw member.

8. The end effector of claim 1, wherein the first slot of the first jaw member is linear along a length thereof.

9. The end effector of claim 8, wherein the second slot of the second jaw member is linear along a length thereof.

10. The end effector of claim 1, wherein the connector pin extends between the first and second jaw members.

11. The end effector of claim 10, wherein the connector pin is spaced apart from the first and second jaw members.

12. The end effector of claim 1, wherein the first and second jaw members are positioned to tip-bias toward one another.

13. An end effector for use and connection to a robotic surgical system including at least one connector member extending from a motor of a control device of the robotic surgical system, the end effector comprising:
 a first movable member including a first drive pin and a first guide pin;
 a second movable member including a second drive pin and a second guide pin;
 a first jaw member defining a first hole and a first slot, the first drive pin of the first movable member received in the first hole of the first jaw member, the second guide pin of the second movable member received in the first slot of the first jaw member; and
 a second jaw member defining a second hole and a second slot, the first guide pin of the first movable member received in the second slot of the second jaw member, the second drive pin of the second movable member received in the second hole of the second jaw member,
 wherein at least one of the first or second movable members is coupled to the at least one connector member of the robotic surgical system, and wherein at least one of the first and second movable members rotates in response to movement of the at least one of the first or second movable members to move at least one of the first and second jaw members relative to the other of the first and second jaw members between open and closed states; and wherein at least one of the first or second movable members includes a pulley.

14. The end effector of claim 13, wherein the first slot of the first jaw member includes a linear portion and a curved portion.

15. The end effector of claim 14, wherein the first jaw member moves in parallel relation to the second jaw member as the second guide pin of the second movable member translates through the linear portion of the first slot of the first jaw member.

16. The end effector of claim 15, wherein the first jaw member pivots about the first drive pin of the first movable member and rotates about a virtual pivot defined between the first and second jaw members as the second guide pin of the second movable member translates through the curved portion of the first slot of the first jaw member.

17. The end effector of claim 14, wherein the second slot of the second jaw member includes a linear portion and a curved portion.

18. The end effector of claim 17, wherein the second jaw member moves in parallel relation to the first jaw member as the first guide pin of the first movable member translates through the linear portion of the second jaw member.

19. The end effector of claim 18, wherein the second jaw member pivots about the second drive pin of the second movable member and rotates about a virtual pivot defined between the first and second jaw members as the first guide pin of the first movable member translates through the curved portion of the second slot of the second jaw member.

20. The end effector of claim 13, wherein the first slot of the first jaw member is linear along a length thereof.

21. The end effector of claim 20, wherein the second slot of the second jaw member is linear along a length thereof.

22. The end effector of claim 13, wherein at least one of the first or second movable members includes first and second links that are axially movable relative to one another to enable the first and second jaw members to move between open and closed states.

* * * * *